United States Patent
Schlienger et al.

(10) Patent No.: US 7,892,234 B2
(45) Date of Patent: Feb. 22, 2011

(54) INTRAMEDULLARY NAIL

(75) Inventors: Andre Schlienger, Basel (CH); Markus Buettler, Oensingen (CH); Peter Senn, Waldenburg (CH)

(73) Assignee: Synthes USA, LLC, West Chester, PA (US)

( * ) Notice: Subject to any disclaimer, the term of this patent is extended or adjusted under 35 U.S.C. 154(b) by 885 days.

(21) Appl. No.: 11/570,674

(22) PCT Filed: Jun. 22, 2004

(86) PCT No.: PCT/CH2004/000379
§ 371 (c)(1),
(2), (4) Date: Jul. 20, 2007

(87) PCT Pub. No.: WO2005/122931
PCT Pub. Date: Dec. 29, 2005

(65) Prior Publication Data
US 2007/0288019 A1  Dec. 13, 2007

(51) Int. Cl.
*A61B 17/56* (2006.01)
*A61B 17/58* (2006.01)
*A61F 2/30* (2006.01)

(52) U.S. Cl. ............... 606/64; 606/62; 623/23.23
(58) Field of Classification Search ............. 606/59, 606/62–68, 95–98, 329; 623/47–56, 23.23, 623/23.33; 411/439, 441, 442
See application file for complete search history.

(56) References Cited

U.S. PATENT DOCUMENTS

| | | | |
|---|---|---|---|
| 2,834,342 A | 5/1958 | Yost | |
| 3,255,747 A | 6/1966 | Cochran et al. | |
| 3,433,220 A | 3/1969 | Zickel | |
| 4,095,591 A | 6/1978 | Graham, Jr. et al. | |
| 4,103,683 A | 8/1978 | Neufeld | |
| 4,172,452 A | 10/1979 | Forte et al. | |
| 4,274,163 A | 6/1981 | Malcom et al. | |

(Continued)

FOREIGN PATENT DOCUMENTS

CH  668 173  12/1988

(Continued)

OTHER PUBLICATIONS

International Preliminary Examination Report for International Application No. PCT/CH04/00379. completed Sep. 21, 2006, German language version.

(Continued)

*Primary Examiner*—Eduardo C Robert
*Assistant Examiner*—Christina Negrelli
(74) *Attorney, Agent, or Firm*—Fay Kaplun & Marcin, LLP

(57) ABSTRACT

An intramedullary nail having a distal end is introducible into a medullary space. A medullary nail segment which is oriented towards the distal end and has a diameter D, a proximal end, at least two cross holes having a borehole axis and a central line formed by a line connecting centers of gravity of the axially successive transversal surfaces orthogonal with respect to the intramedullary nail, without taking into account the cross holes. The borehole axis of at least one cross-hole is shifted at a gap $d_1 > 0$ with respect to the central line.

19 Claims, 2 Drawing Sheets

U.S. PATENT DOCUMENTS

| | | | |
|---|---|---|---|
| 4,438,762 A | 3/1984 | Kyle | |
| 4,494,535 A | 1/1985 | Haig | |
| 4,612,920 A | 9/1986 | Lower | |
| 4,621,628 A | 11/1986 | Brudermann | |
| 4,622,959 A | 11/1986 | Marcus | |
| 4,657,001 A | 4/1987 | Fixel | |
| 4,697,585 A | 10/1987 | Williams | |
| 4,705,027 A | 11/1987 | Klaue | |
| 4,754,749 A | 7/1988 | Tsou | |
| 4,776,330 A | 10/1988 | Chapman et al. | |
| 4,791,918 A | 12/1988 | Von Hasselbach | |
| 4,805,607 A | 2/1989 | Engelhardt et al. | |
| 4,817,591 A | 4/1989 | Klaue | |
| 4,858,602 A | 8/1989 | Seidel et al. | |
| 4,875,474 A | 10/1989 | Border | |
| 4,973,332 A | 11/1990 | Kummer | |
| 5,032,125 A | 7/1991 | Durham et al. | |
| 5,041,114 A | 8/1991 | Chapman et al. | |
| 5,041,115 A | 8/1991 | Frigg et al. | |
| 5,120,171 A | 6/1992 | Lasner | |
| 5,167,663 A | 12/1992 | Brumfield | |
| 5,176,681 A | 1/1993 | Lawes et al. | |
| 5,300,074 A | 4/1994 | Frigg | |
| 5,312,406 A | 5/1994 | Brumfield | |
| 5,364,398 A | 11/1994 | Chapman et al. | |
| 5,374,235 A | 12/1994 | Ahrens | |
| 5,454,813 A | 10/1995 | Lawes | |
| 5,472,444 A * | 12/1995 | Huebner et al. | 606/64 |
| 5,484,439 A | 1/1996 | Olson et al. | |
| 5,549,610 A | 8/1996 | Russell et al. | |
| 5,573,536 A | 11/1996 | Grosse et al. | |
| 5,578,035 A | 11/1996 | Lin | |
| 5,591,168 A | 1/1997 | Judet et al. | |
| 5,658,287 A | 8/1997 | Hofmann et al. | |
| 5,658,339 A | 8/1997 | Tronzo et al. | |
| 5,713,901 A | 2/1998 | Tock | |
| 5,713,902 A | 2/1998 | Friedl | |
| 5,728,099 A | 3/1998 | Tellman et al. | |
| 5,741,256 A | 4/1998 | Bresina | |
| 5,772,662 A | 6/1998 | Chapman et al. | |
| 5,908,422 A | 6/1999 | Bresina | |
| 5,928,235 A | 7/1999 | Friedl | |
| 5,935,127 A | 8/1999 | Border | |
| 5,976,139 A | 11/1999 | Bramlet | |
| 6,010,506 A | 1/2000 | Gosney et al. | |
| 6,059,785 A | 5/2000 | Schavan et al. | |
| 6,123,708 A | 9/2000 | Kilpela et al. | |
| 6,126,661 A | 10/2000 | Faccioli et al. | |
| 6,187,007 B1 | 2/2001 | Frigg et al. | |
| 6,197,065 B1 | 3/2001 | Martin et al. | |
| 6,200,685 B1 | 3/2001 | Davidson | |
| 6,261,290 B1 | 7/2001 | Friedl | |
| 6,296,645 B1 | 10/2001 | Hover et al. | |
| 6,454,810 B1 | 9/2002 | Lob | |
| 7,182,765 B2 | 2/2007 | Roth et al. | |
| 2002/0103488 A1 | 8/2002 | Lower et al. | |
| 2002/0151898 A1 | 10/2002 | Sohngen et al. | |
| 2002/0173792 A1 | 11/2002 | Severns et al. | |
| 2003/0069581 A1 | 4/2003 | Stinson et al. | |
| 2003/0114855 A1 | 6/2003 | Wahl et al. | |
| 2006/0064095 A1 | 3/2006 | Senn et al. | |
| 2006/0111716 A1 | 5/2006 | Schlienger et al. | |
| 2006/0149248 A1 | 7/2006 | Schlienger et al. | |
| 2006/0161155 A1 | 7/2006 | Schlienger et al. | |
| 2006/0189988 A1 | 8/2006 | Schlienger et al. | |
| 2006/0235395 A1 | 10/2006 | Frigg et al. | |
| 2006/0241605 A1 | 10/2006 | Schlienger et al. | |

FOREIGN PATENT DOCUMENTS

| | | |
|---|---|---|
| CH | 674 613 | 6/1990 |
| DE | 196 29 011 A1 | 1/1998 |
| DE | 199 45 611 A1 | 9/2001 |
| EP | 0 251 583 A2 | 1/1988 |
| EP | 0 321 170 B1 | 6/1989 |
| EP | 0 381 462 A2 | 8/1990 |
| EP | 0 411 273 A1 | 2/1991 |
| EP | 0 471 418 A1 | 2/1992 |
| EP | 0 838 199 A1 | 4/1998 |
| EP | 0 845 245 A2 | 6/1998 |
| EP | 0 853 923 A1 | 7/1998 |
| EP | 0 882 431 A1 | 12/1998 |
| EP | 0 919 200 A1 | 6/1999 |
| EP | 0 968 685 A2 | 6/1999 |
| EP | 1 024 762 B1 | 8/2000 |
| EP | 1 053 718 A1 | 11/2000 |
| EP | 1 214 914 A2 | 6/2002 |
| EP | 1 260 188 A1 | 11/2002 |
| FR | 2 784 283 | 4/2000 |
| GB | 2209947 A | 6/1989 |
| JP | 09-066059 | 3/1997 |
| JP | 09-066060 | 3/1997 |
| JP | 09-066061 | 3/1997 |
| JP | 11-137566 | 5/1999 |
| JP | 2000-051224 | 2/2000 |
| JP | 2000-051225 | 2/2000 |
| JP | 2000-342596 | 12/2000 |
| WO | WO 93/15679 | 8/1993 |
| WO | WO 96/15737 | 5/1996 |
| WO | WO 97/37606 | 10/1997 |
| WO | WO 98/05263 | 2/1998 |
| WO | WO 98/30164 | 7/1998 |
| WO | WO 98/41161 | 9/1998 |
| WO | WO 98/46169 | 10/1998 |
| WO | WO 99/20195 | 4/1999 |
| WO | WO 99/20195 A1 | 4/1999 |
| WO | WO 00/44946 | 8/2000 |
| WO | WO 00/67653 | 11/2000 |
| WO | WO 02/060331 | 8/2002 |
| WO | WO 03/015649 | 2/2003 |
| WO | WO 03/101320 | 12/2003 |
| WO | WO 03/101320 A1 | 12/2003 |
| WO | WO 2004/082494 | 9/2004 |
| WO | WO 2004/082494 A1 | 9/2004 |

OTHER PUBLICATIONS

International Preliminary Examination Report for International Application No. PCT/CH04/00379, completed Sep. 21, 2006, English language translation of the German language version.

Wilkey et al., *Mechanical Characteristics of Eight Femoral Intramedullary Nailing Systems*, Journal of Orthopaedic Trauma, ISSN: 0890-5339, Mar./Apr. 1998, pp. 177-185, vol. 12, No. 3.

International Search Report of PCT/CH2004/000379.

* cited by examiner

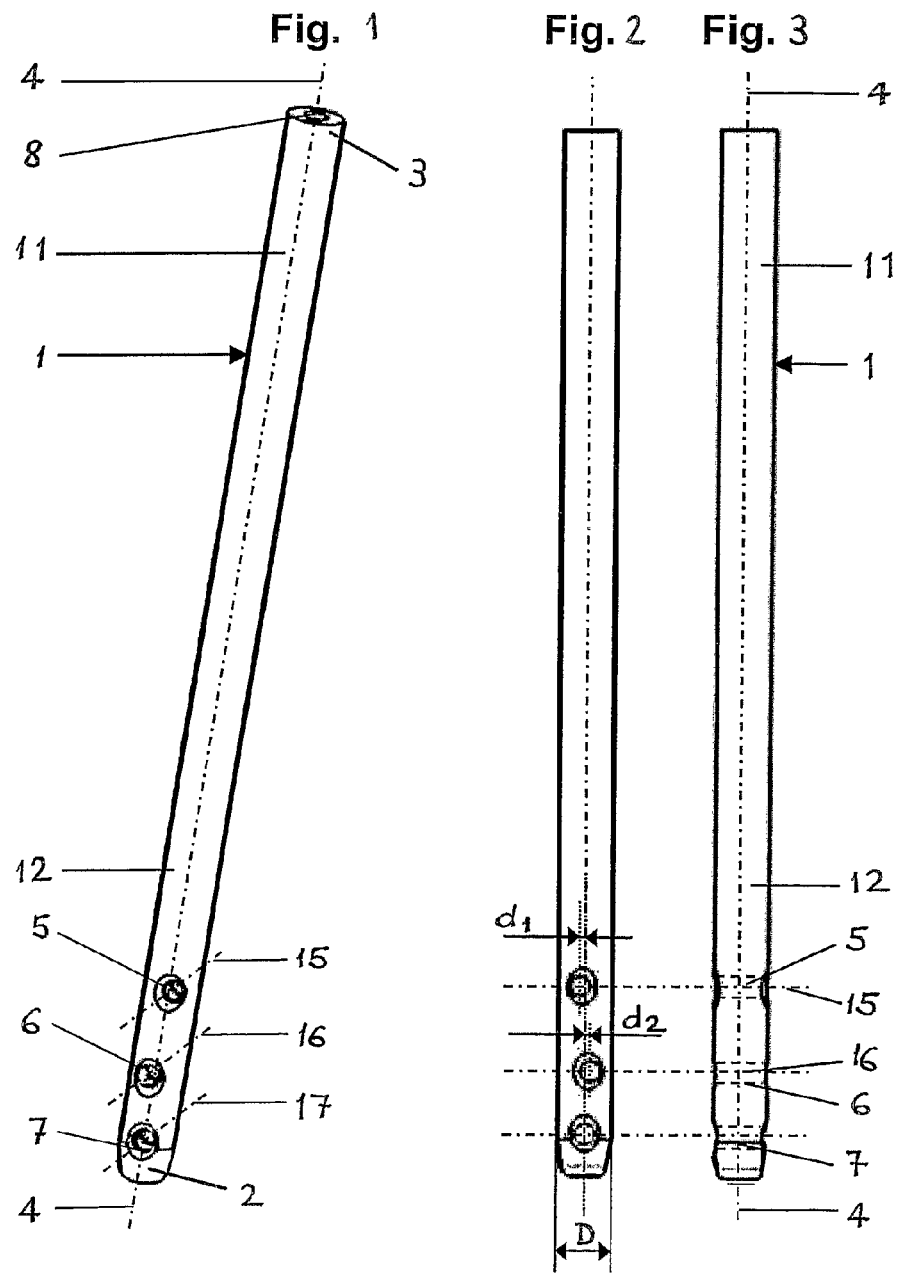

INTRAMEDULLARY NAIL

RELATED APPLICATION DATA

This application is the U.S. National Stage application of International Application No. PCT/CH2004/000379, filed Jun. 22, 2004.

FIELD OF THE INVENTION

The invention concerns an intramedullary nail for use in repairing bone fractures and, more particularly, an intramedullary nail for use in repairing fractures of the distal tibia.

BACKGROUND OF THE INVENTION

An intramedullary nail of this kind is known from European patent publication EP 1 024 762 to LEU. This known intramedullary nail comprises several transversal distal holes, whose borehole axes all cross the intramedullary nail's central line. The disadvantage of this transversal hole setup is that the introduction of the force for the forces to be transmitted through the intramedullary nail occurs in a bone volume whose dimensions transversal to the central axis are limited to the diameter of the locking screws and are therefore stressing the same bone fibres in a longitudinal direction.

SUMMARY OF THE INVENTION

The invention intends to provide a remedy for this situation. The task of the invention is to create an intramedullary nail which allows a high degree of locking stability and introduction of force, for the forces to be transmitted across the intramedullary nail that is optimally distributed over the cross section of the bone.

The invention solves the proposed task by an intramedullary nail comprising a longitudinal nail body having a total length, a distal stem portion and a proximal portion the distal stem portion having an outer diameter D and configured and dimensioned for insertion into a medullary canal of a bone. The longitudinal nail body defines a central longitudinal axis coaxial with a line connecting a first center of gravity of a first transverse cross-section taken through the nail body orthogonal to the central longitudinal axis with a second center of gravity of a second transverse cross-section taken through the nail body orthogonal to the central longitudinal axis. At least a first through-hole and a second through-hole are formed in the distal stem portion transverse to the central longitudinal axis, the first through-hole having a radius $R_1$ and defining a first central hole axis transverse to the central longitudinal axis and the second through-hole having a radius $R_2$ and defining a second central hole axis transverse to the central longitudinal axis. At least one of the first and second central holes axes is offset a distance $d_1>0$ from the central longitudinal axis of the nail body, and $(d_1+R_1)<(D/2)$, such that the mantle surfaces of each of the two through-holes are wholly inside the intramedullary nail body.

The advantages attained by the invention are essentially to be seen in the fact that thanks to the intramedullary nail according to the invention:

The locking stability is boosted by the additional asymmetry of the distal locking mechanism;
The introduction of the forces to be transmitted across the intramedullary nail is optimally distributed over the cross section of the bone; and
The same bone fibres are not stressed in a longitudinal direction.

In a special form of embodiment the borehole axes of at least two cross holes exhibit distances $d_1>0$ and $d_2>0$ with respect to the central line.

In another form of embodiment, the borehole axes of the at least two cross holes run past the central line on opposite sides. The advantage of this embodiment is based on the fact that the bone screws capable of being introduced in both cross holes are not stressing the same bone fibre of the tubular bone.

In a further form of embodiment the borehole axis of the at least one cross hole is set in a plane orthogonal to the central line at a distance $d_1$.

In an additional form of embodiment, the distances $d_1$ and $d_2$ are, with respect to the diameter D, in a range of 0.0001 D<d<0.6000 D, and preferably in a range of 0.2 D<d<0.5 D, respectively.

In another form of embodiment the intramedullary nail includes a channel coaxial to the central line.

The orthogonal cross-sectional surfaces of the intramedullary nail can preferably be conformed in a circular or circle-shaped form.

In a special form of embodiment the at least two cross holes are placed in the distal half of the intramedullary nail.

The distance d is advantageously larger than 0.5 mm and preferably larger than 1.0 mm. However, the distance $d_1$ is properly smaller than 0.5 mm and preferably smaller than 3.5 mm. The distance $d_1$ depends up to a certain point on the diameter of the intramedullary nail. The $D/d_1$ ratio between the diameter D of the intramedullary nail and the distance $d_1$ should therefore properly be larger than 5, preferably larger than 8. On the other hand, the $D/d_1$ ratio between the diameter D of the intramedullary nail and the distance $d_1$ should properly be smaller than 25, preferably smaller than 21.

In another form of embodiment, the mantle surfaces of the at least two cross holes are fully embedded inside the intramedullary nail, meaning that the cross holes open only when entering and leaving the intramedullary nail, and are for the rest wholly extended inside the intramedullary nail.

BRIEF DESCRIPTION OF THE DRAWINGS

The invention and developments of the invention will be clarified in further detail below, by using schematic representations of several examples of preferred embodiments.

The figures show:

FIG. 1 is a perspective view of an intramedullary nail according to a preferred embodiment of the invention;

FIG. 2 is a side view of the intramedullary nail according to FIG. 1;

FIG. 3 is a side view of the intramedullary nail according to a preferred embodiment of the invention, turned 90° with respect to FIG. 2;

DETAILED DESCRIPTION OF THE PREFERRED EMBODIMENTS

Figure 4:
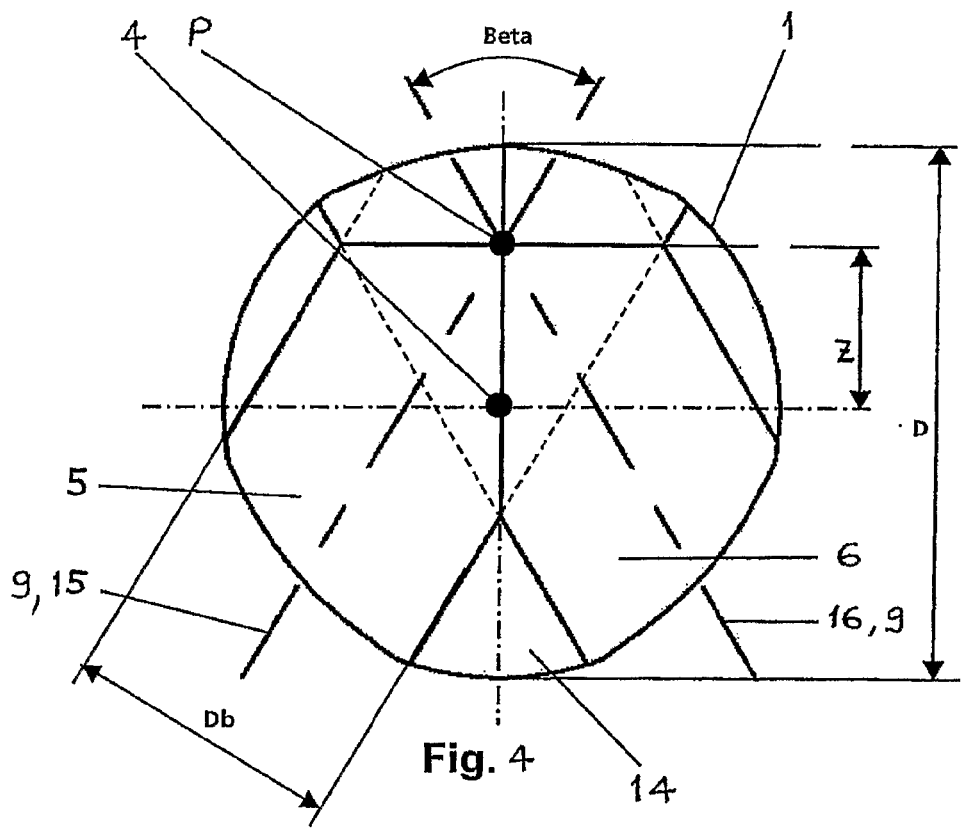
FIG. 4 is an orthogonal cross section view across an intramedullary nail modified with respect to the medullary nail according to FIG. 1-3.

The form of embodiment of an intramedullary nail shown in FIG. 1-3 has a proximal half 11, a distal half 12 suitable for introducing it into the medullary, channel, and a central line 4. The intramedullary nail 1 exhibits an essentially constant diameter D and is penetrated by a channel 8 from its proximal end 3 to its distal end 2. The distal half presents three cross holes capable of receiving locking screws 5, 6, 7 (not shown).

The most proximally situated cross hole 5 has a borehole axis 15, the middle cross hole 6 has a borehole axis 16 and the most distal cross hole 7 a borehole axis 17. The cross holes 5, 6, 7 are arranged so that their borehole axes 15; 16; 17 are parallel to each other. The diameter of the intramedullary nail 1 amounts to D=10 mm. The borehole axis 15 of the cross hole 5 has a distance $d_1$=0.5 mm with respect to the central line 4. The borehole axis 16 of the cross hole 6 also has a distance $d_2$=0.5 mm with respect to the central axis 4, but on the opposite side. Only the cross hole set in the most distal position 7 has a borehole axis 17 that intersects the central line 4. The most proximal and the middle cross holes 5, 6 are offset with respect to the perimeter of the intramedullary nail 1 only to the degree of not piercing the outer mantle surface of the intramedullary nail 1.

Figure 5:
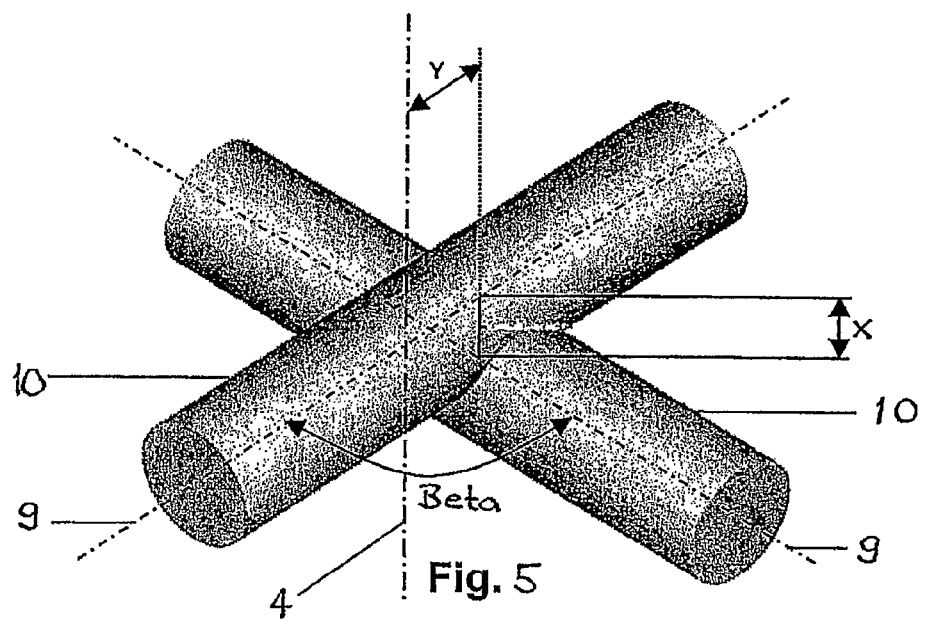
FIG. 5 is a perspective view of the virtual borehole cylinder of another form of embodiment of the intramedullary nail.

FIG. 4 shows a further form of embodiment of the intramedullary nail 17 which differs from the form of embodiment shown in FIG. 1-3 in that the virtual borehole cylinders 10 of two adjacent cross holes 5, 6—just like in the form of embodiment according to FIG. 5—penetrate each other. The cylinder axes 9 of both virtual borehole cylinders 10 correspond to the borehole axes 15; 16 of the two cross holes 5; 6 and intersect each other in point P, which has a distance z=0.4 D from the central line 4. In other words, the point P does not fall on the central line 4 of the intramedullary nail. The virtual borehole cylinders 10 have two separate inlets in the intramedullary nail 1, but only one common outlet from the intramedullary nail. The cylinder axes 9 of the two virtual borehole cylinders 10 fall into a plane orthogonal to the central line 4, which corresponds to the drawing plane of FIG. 4. The cylinder axes 9 of the two virtual borehole cylinders 10 can however also lie in a plane which is penetrated by the longitudinal axis 4 under an angle deviating from 90°.

In the example shown, the cylinder axes 9 of the two virtual borehole cylinder 10 cross each other under an angle β of 60°. In the example shown, the diameter $D_b$ of the virtual borehole cylinder 10 in the example is equal to 0.3 times D.

FIG. 5 shows another form of embodiment of the intramedullary nail 1, wherein the cylinder axes 9 of the two virtual borehole cylinders 10 can also run at an oblique angle and have the shortest distance x to each other which is smaller than half the sum of the two diameters $D_b$ of the virtual borehole cylinder 10. In the example shown here, the shortest distance x between the two oblique cylinder axes 9 runs parallel to the longitudinal axis 4 and has a shortest distance y>0 to the same. However, the length defined by the shortest distance x can also run obliquely to the longitudinal axis 4. The distance y is in the range of D/2>y>0.4 D. The cylinder axes 9 of the two virtual borehole cylinders 10 separate at this point under an angle β of 90°.

The invention claimed is:

1. An intramedullary nail comprising:
    a longitudinal nail body having a total length, a distal stem portion and a proximal portion, the distal stem portion having an outer diameter D and configured and dimensioned for insertion into a medullary canal of a bone, and the longitudinal nail body defining a central longitudinal axis coaxial with a line connecting a first center of gravity of a first transverse cross-section taken through the nail body orthogonal to the central longitudinal axis with a second center of gravity of a second transverse cross-section taken through the nail body orthogonal to the central longitudinal axis; and
    at least a first through-hole and a second through-hole formed in the distal stem portion transverse to the central longitudinal axis, the first through-hole having a radius $R_1$ and defining a first central hole axis transverse to the central longitudinal axis and the second through-hole having a radius $R_2$ and defining a second central hole axis transverse to the central longitudinal axis;
    wherein at least one of the first and second central holes axes is offset a distance $d_1$>0 from the central longitudinal axis of the nail body, and $(d_1+R_1)<(D/2)$.

2. The device of claim 1, wherein the first central hole axis is offset a distance $d_1$>0 from the central longitudinal axis of the nail body and the second central hole axis is offset a distance $d_2$>0 from the central longitudinal axis of the nail body, where $(d_2+R_2)<(D/2)$.

3. The device of claim 2, wherein the first central hole axis is offset on a first side of the central longitudinal axis and the second central hole axis is offset on a second side of the central longitudinal axis.

4. The device of claim 2, wherein the magnitude of the distances $d_1$ and $d_2$ relative to the diameter D are in a range of 0.0001 D<d<0.6000 D.

5. The device of claim 2, wherein the magnitude of the distances $d_1$ and $d_2$ relative to the diameter D are in a range of 0.2 D<d<0.5 D.

6. The device of claim 1, wherein the nail body further includes a longitudinal bore coaxial with the central longitudinal axis.

7. The device of claim 1, wherein the first and second transverse cross-sections are substantially circular in shape.

8. The device of claim 1, wherein the distance $d_1$ is greater than 0.5 mm.

9. The device of claim 1, wherein the distance $d_1$ is greater than 1.0 mm.

10. The device of claim 1, wherein the distance $d_1$ is less than 5.0 mm.

11. The device of claim 1, wherein the distance $d_1$ is less than 3.5 mm.

12. The device of claim 1, wherein the ratio of $D/d_1$ is greater than 5.

13. The device of claim 1, wherein the ratio of $D/d_1$ is greater than 8.

14. The device of claim 1, wherein the ratio of $D/d_1$ is less than 25.

15. The device of claim 1, wherein the ratio of $D/d_1$ is less than 21.

16. A bone fixation method comprising:
    inserting an intramedullary nail into a medullary canal of a bone, the nail including
        a longitudinal nail body having a total length, a distal stem portion and a proximal portion, the distal stem portion having an outer diameter D, and the longitudinal nail body defining a central longitudinal axis coaxial with a line connecting a first center of gravity of a first transverse cross-section taken through the nail body orthogonal to the central longitudinal axis with a second center of gravity of a second transverse cross-section taken through the nail body orthogonal to the central longitudinal axis, and
        at least a first through-hole and a second through-hole formed in the distal stem portion transverse to the central longitudinal axis, the first through-hole having a radius $R_1$ and defining a first central hole axis transverse to the central longitudinal axis and the second through-hole having a radius $R_2$ and defining a second central hole axis transverse to the central longitudinal axis, wherein at least one of the first and second central holes axes is offset a distance $d_1$>0 from the central longitudinal axis of the nail body, and $(d_1+R_1)<(D/2)$; and inserting a bone fastener through at least one of the first and second through-holes in the distal portion of the nail body, offset from the central longitudinal axis.

17. The method of claim 16, wherein the first central hole axis is offset a distance $d_1>0$ from the central longitudinal axis of the nail body and the second central hole axis is offset a distance $d_2>0$ from the central longitudinal axis of the nail body, where $(d_2+R_2)<(D/2)$.

18. The method of claim 17, wherein the first central hole axis is offset on a first side of the central longitudinal axis and the second central hole axis is offset on a second side of the central longitudinal axis.

19. The method of claim 17, wherein the magnitude of the distances $d_1$ and $d_2$ relative to the diameter D are in a range of $0.2\,D<d<0.5\,D$.

* * * * *